(12) United States Patent
Hsieh

(10) Patent No.: US 12,349,920 B2
(45) Date of Patent: *Jul. 8, 2025

(54) TOURNIQUET HAVING UNEVEN SURFACES

(71) Applicant: WHEELSTONE ENTERPRISE CO., LTD., Taichung (TW)

(72) Inventor: Yung-Lin Hsieh, Taichung (TW)

(73) Assignee: Wheelstone Enterprise Co., Ltd., Taichung (TW)

( * ) Notice: Subject to any disclaimer, the term of this patent is extended or adjusted under 35 U.S.C. 154(b) by 341 days.

This patent is subject to a terminal disclaimer.

(21) Appl. No.: 18/076,525

(22) Filed: Dec. 7, 2022

(65) Prior Publication Data

US 2024/0188964 A1 Jun. 13, 2024

(51) Int. Cl.
*A61B 17/132* (2006.01)

(52) U.S. Cl.
CPC ................... *A61B 17/132* (2013.01)

(58) Field of Classification Search
CPC .............. A61B 17/132; A61B 17/1322; A61B 17/1325; A61B 2017/00858; A61B 2017/00862; A61B 90/92; A61B 5/6831; A61F 13/0273; A61F 13/0203; A61F 13/0243; A61F 2013/0028; A61F 13/00051; A61F 13/0226; A61F 13/0246; A61F 2013/00127; A61F 13/01038; A61F 13/05; A61F 13/08; A61F 5/0111; A61F 13/0206; A61F 15/008; A61F 2013/00119; A61F 13/01017; A61F 2013/00468; A61F 13/066; A61F 5/30; A61F 13/00; A61F 13/64; A61F 2013/00604; A61F 2013/00608; A61F 2013/00702; A61F 2013/00238; A61F 13/01; A61F 13/01008; A61F 13/108; A61F 2007/0228; A61F 2013/00097; A41D 2400/38; A41D 13/0015; A41D 31/18; A41D 1/08; A41D 20/00; A61H 1/008; A45F 3/14; A41B 2400/38; A41B 9/14; A41F 9/00; A41F 9/02; A41F 9/025; A41C 3/12; A41C 3/0057; A63B 21/0552;

(Continued)

(56) References Cited

U.S. PATENT DOCUMENTS 3,051,179 A * 8/1962 Dwyer ............... A61B 17/1327
                                                           81/64
3,097,644 A * 7/1963 Parker ................... A61F 13/041
                                                          206/440

(Continued)

FOREIGN PATENT DOCUMENTS

TW M596608 U * 6/2020 ............. A61F 5/042

*Primary Examiner* — Tan-Uyen T Ho
*Assistant Examiner* — Bridget E. Rabaglia

(57) ABSTRACT

A tourniquet includes an elastic band including uneven top and bottom surface. The uneven surface includes rows of a plurality of spaced first uneven zones and rows of a plurality of spaced second uneven zones. The first uneven zone is disposed between two adjacent ones of the second uneven zone. The second uneven zone is disposed between two adjacent ones of the first uneven zone. The first and second uneven zones are concave rectangular. Each uneven zone includes two raised, opposite inclined edges and the other two raised, opposite inclined edges. A ridge is formed between two adjacent inclined edges of different uneven zones.

8 Claims, 8 Drawing Sheets

(58) Field of Classification Search
CPC ............ A63B 21/0555; A63B 21/4025; A63B 21/4043
See application file for complete search history.

(56) References Cited

U.S. PATENT DOCUMENTS

| | | | |
|---|---|---|---|
| 10,736,640 B2 * | 8/2020 | Hsieh | ................. A61B 17/1322 |
| 2020/0046371 A1 * | 2/2020 | Hsieh | ................. A61B 17/1322 |

* cited by examiner

TOURNIQUET HAVING UNEVEN SURFACES

FIELD OF THE INVENTION

The invention relates to tourniquets and more particularly to a tourniquet having uneven top and bottom surfaces for increasing friction and slip resistance when the tourniquet is applied to the body part.

BACKGROUND OF THE INVENTION

Referring to FIG. 9, a conventional tourniquet 1 made of rubber is shown. The tourniquet 1 has a texture 2 on each of top and bottom surfaces. The textures 2 are formed by adhering two woven fabrics on two surfaces of a material (e.g., nylon or polyester fiber), sulfurizing same, and separating the woven fabrics from the material. While the textures 2 are slip resistant, changes of short side and long side of the tourniquet 1 are the same when a pulling force is exerted on the short and long sides thereof due to oblique, crossing patterns of the textures 2. As a result, it does little to the improvement of extension of the tourniquet 1.

Thus, the need for improvement still exists.

SUMMARY OF THE INVENTION

It is therefore one object of the invention to provide a tourniquet comprising an elastic band including an uneven surface on each of top and bottom surfaces, the uneven surfaces and the elastic band being formed integrally, each of the uneven surfaces including a plurality of rows of a plurality of spaced first uneven zones and a plurality of rows of a plurality of spaced second uneven zones, the first uneven zone being disposed between two adjacent ones of the second uneven zone, and the second uneven zone being disposed between two adjacent ones of the first uneven zone; wherein the first uneven zones are substantially rectangular and concave toward its center; each of the first uneven zones include two raised, opposite first inclined edges, two raised, opposite second inclined edges, and four corners; length of the second inclined edge is greater than that of the first inclined edge; height of the first inclined edge is greater than that of the second inclined edge; the second inclined edges and the elastic band are oriented lengthwise; the second inclined edges are parallel to one another; extent of an elastic deformation of the second inclined edge is greater than that of the first inclined edge; the second uneven zone is surrounded by two second inclined edges of two adjacent first uneven zones of the same row and two first inclined edges of two adjacent first uneven zones of two spaced rows of the first uneven zones; the second uneven zones are substantially rectangular and concave toward its center; each of the second uneven zones include two raised, opposite third inclined edges and two raised, opposite fourth inclined edges; a first ridge is formed between the first inclined edge and the second inclined edge; a second ridge is formed between the second inclined edge and the fourth inclined edge; height of the first ridge is greater than that of the second ridge; length of the fourth inclined edge is greater than that of the third inclined edge; the concave first uneven zone has a first depth; the concave second uneven zone has a second depth; and the first depth is greater than the second depth.

The invention has the following advantages and benefits in comparison with the conventional art: the second inclined edges are oriented in a direction the same as the extension direction of the elastic band. The second inclined edges are parallel one another. Extent of an elastic deformation of the second inclined edge is greater than that of the first inclined edge. A greater force is required to apply to the short edges of the elastic band when force is applied to the elastic band. But a greater force is not required to apply to the long edges of the elastic band when force is applied to the elastic band. This structure allows a user to pull the elastic band along its lengthwise direction to extend the elastic band. Thus, the first inclined edges become shorter. A plurality of widthwise, curved lines are formed on either surface of the elastic band. Thus, the surfaces of the elastic band are significantly uneven. As a result, friction and slip resistance of the elastic band are increased greatly when the elastic band is fastened.

The above and other objects, features and advantages of the invention will become apparent from the following detailed description taken with the accompanying drawings

DETAILED DESCRIPTION OF THE INVENTION

Figure 1:
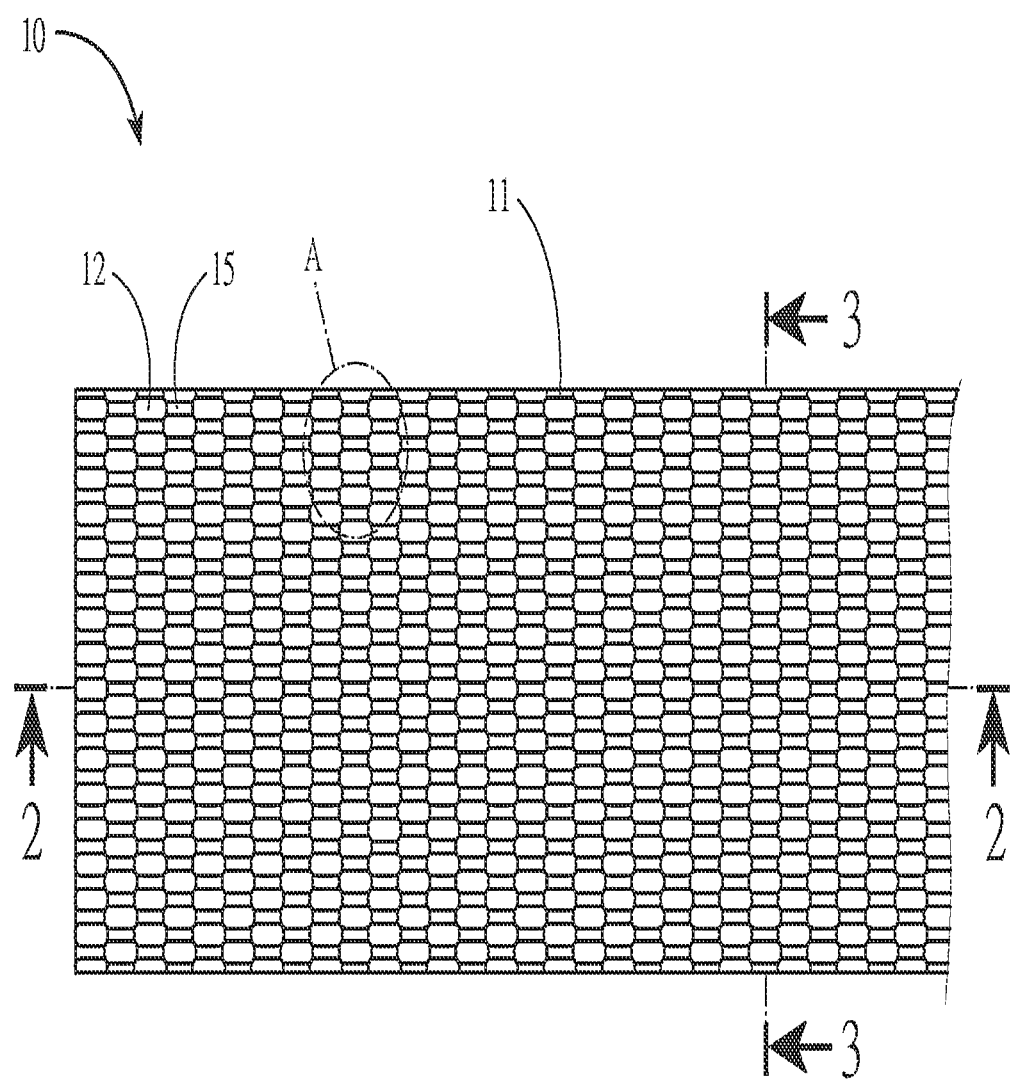
FIG. 1 is a plan view of a tourniquet of the invention.
Figure 2:
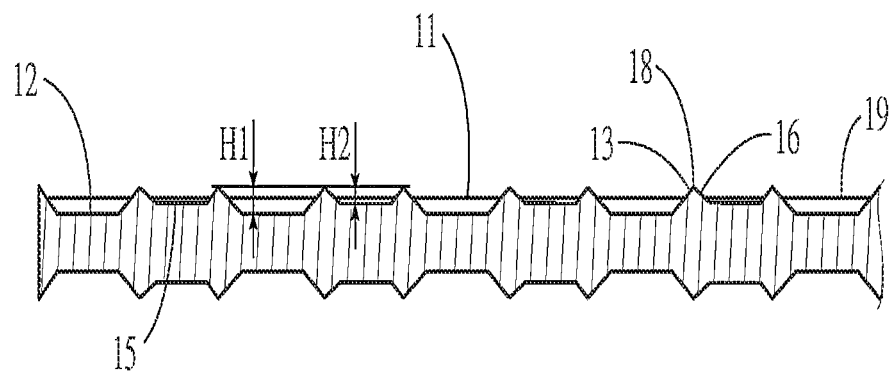
FIG. 2 is a sectional view taken along line 2-2 of FIG. 1.
Figure 3:
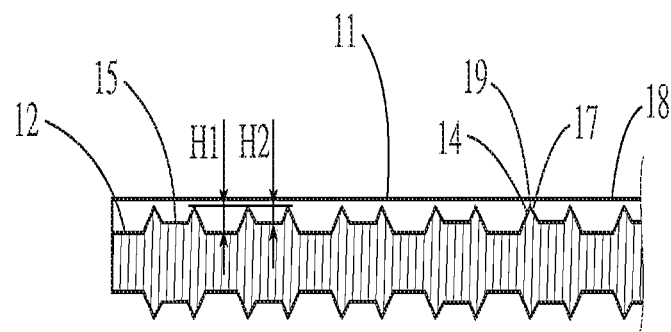
FIG. 3 is a sectional view taken along line 3-3 of FIG. 1.

Referring to FIGS. 1 to 4, a tourniquet in accordance with the invention comprises the following components as discussed in detail below.

An elastic band 10 has uneven top and bottom surfaces. The elastic band 10 is elongated. The elastic band 10 includes an uneven surface 11 on each of the top and the bottom. The uneven surfaces 11 and the elastic band 10 are formed of the same material (e.g., synthetic rubber). Further, the uneven surfaces 11 and the elastic band 10 are formed integrally. The uneven surface 11 includes rows of a plurality of spaced first uneven zones 12 and rows of a plurality of spaced second uneven zones 15 in which the first uneven zone 12 is disposed between two adjacent ones of the second uneven zone 15 and the second uneven zone 15 is disposed between two adjacent ones of the first uneven zone 12. The first uneven zone 12 is substantially rectangular and concave toward its center. The first uneven zone 12 includes two raised, opposite first inclined edges 13, two raised, opposite second inclined edges 14, and four curved corners. Length of the second inclined edge 14 is greater than that of the first inclined edge 13. Height of the first inclined edge 13 is greater than that of the second inclined edge 14. The second inclined edges 14 and the elastic band 10 are oriented lengthwise. The second inclined edges 14 are parallel to one another. Extent of an elastic deformation of the second inclined edge 14 is greater than that of the first inclined edge 13.

Specifically, the second uneven zone 15 is surrounded by two second inclined edges 14 of two adjacent first uneven zones 12 of the same row and two first inclined edges 13 of two adjacent first uneven zones 12 of two spaced rows of the first uneven zones 12. The second uneven zone 15 is substantially rectangular and concave toward its center. The second uneven zone 15 includes two raised, opposite third inclined edges 16 and two raised, opposite fourth inclined edges 17. Length of the fourth inclined edge 17 is greater than that of the third inclined edge 16. The concave first uneven zone 12 has a first depth H1, the concave second uneven zone 15 has a second depth H2, and the first depth H1 is greater than the second depth H2. The length of the third inclined edge 16 is less than that of the first inclined edge 13, the length of the fourth inclined edge 17 is less than that of the second inclined edge 14, and the length of the fourth inclined edge 17 is greater than that of the first inclined edge 13. A first ridge 18 is formed between the first inclined edge 13 and the third inclined edge 16, a second ridge 19 is formed between the second inclined edge 14 and the fourth inclined edge 17, and height of the first ridge 18 is greater than that of the second ridge 19.

Figure 4:
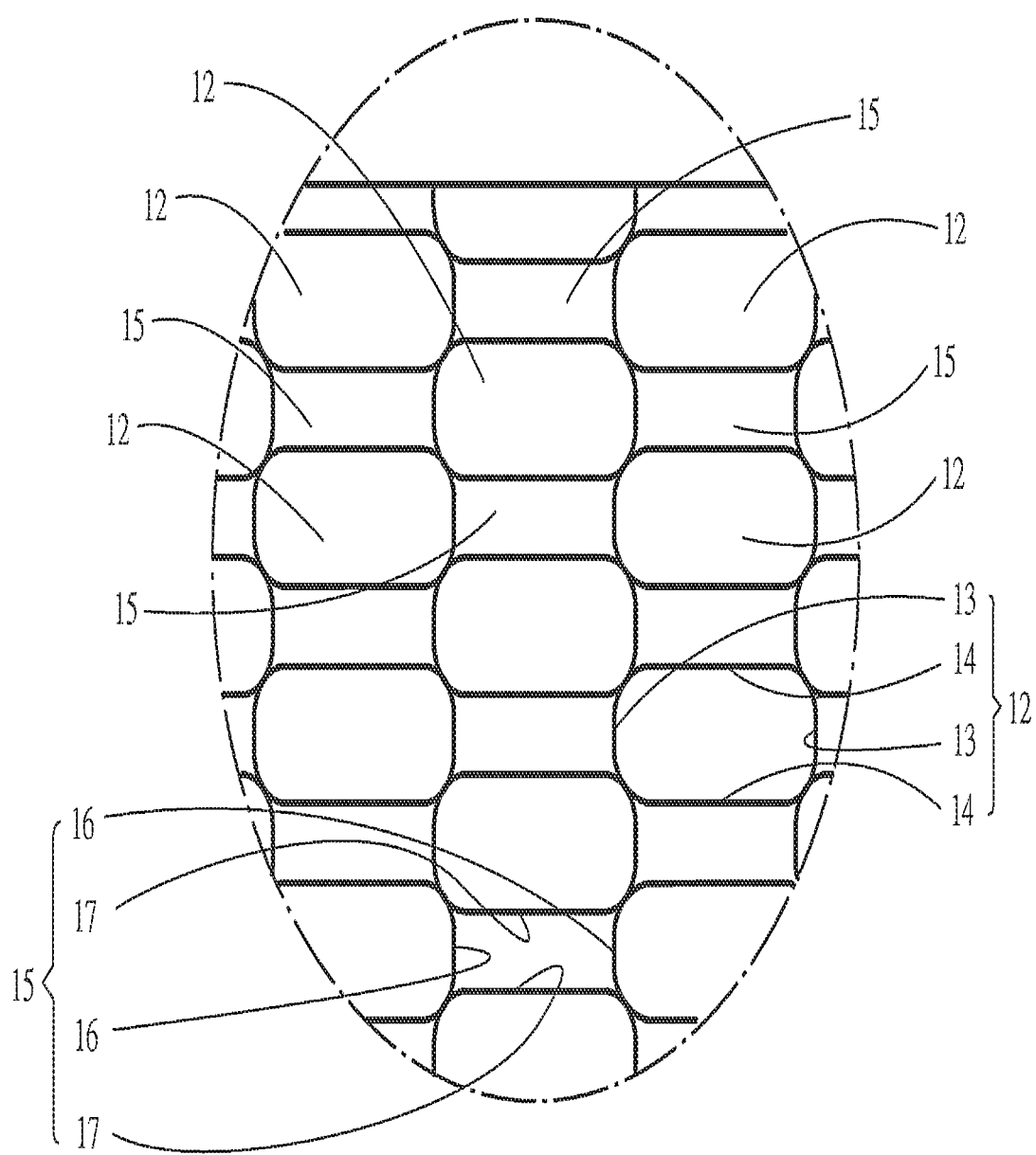
FIG. 4 is a detailed view of the area in circle A of FIG. 1.
Figure 5:
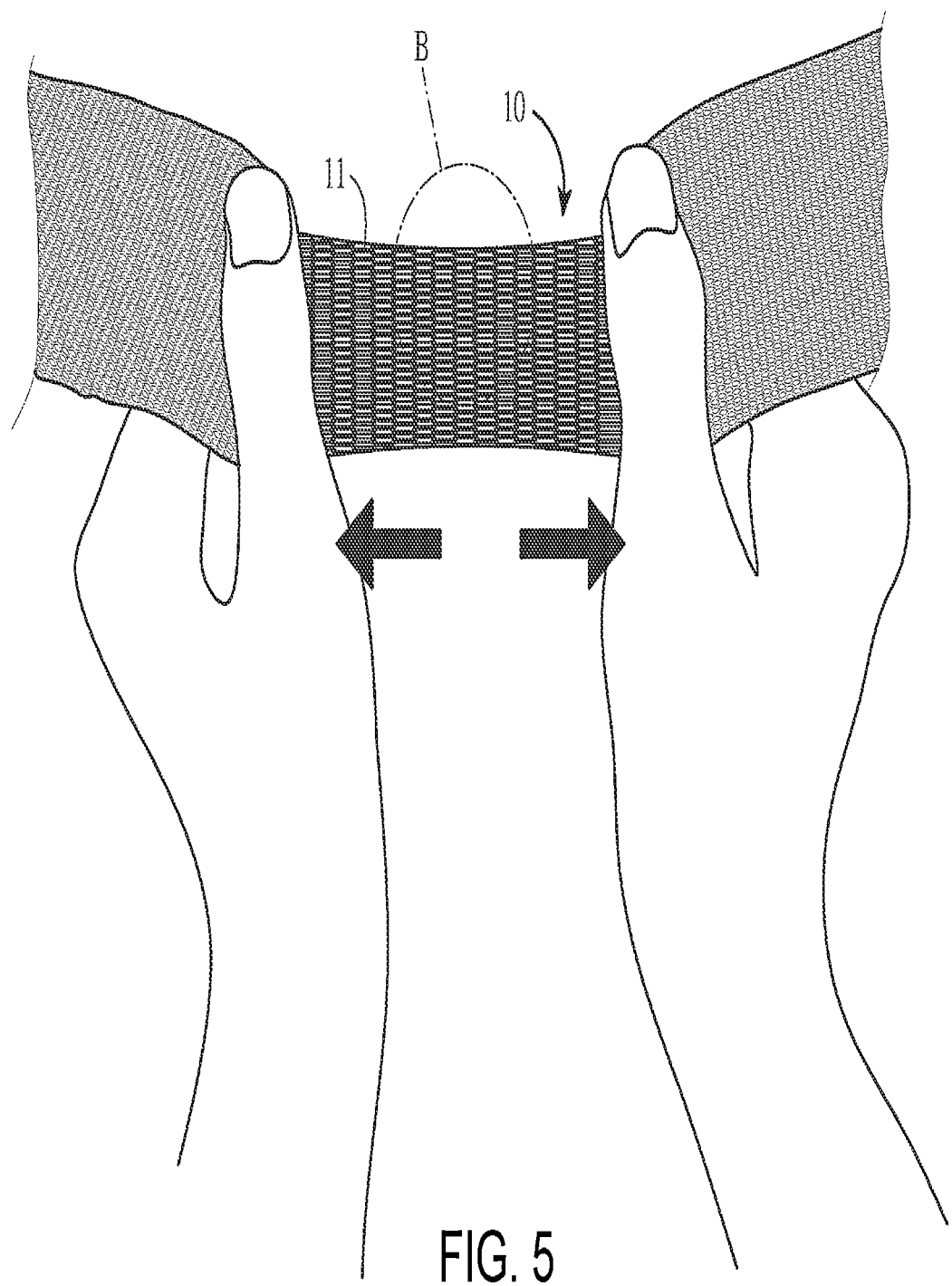
FIG. 5 schematically depicts the tourniquet being extended in response to a pulling force exerted lengthwise.
Figure 6:
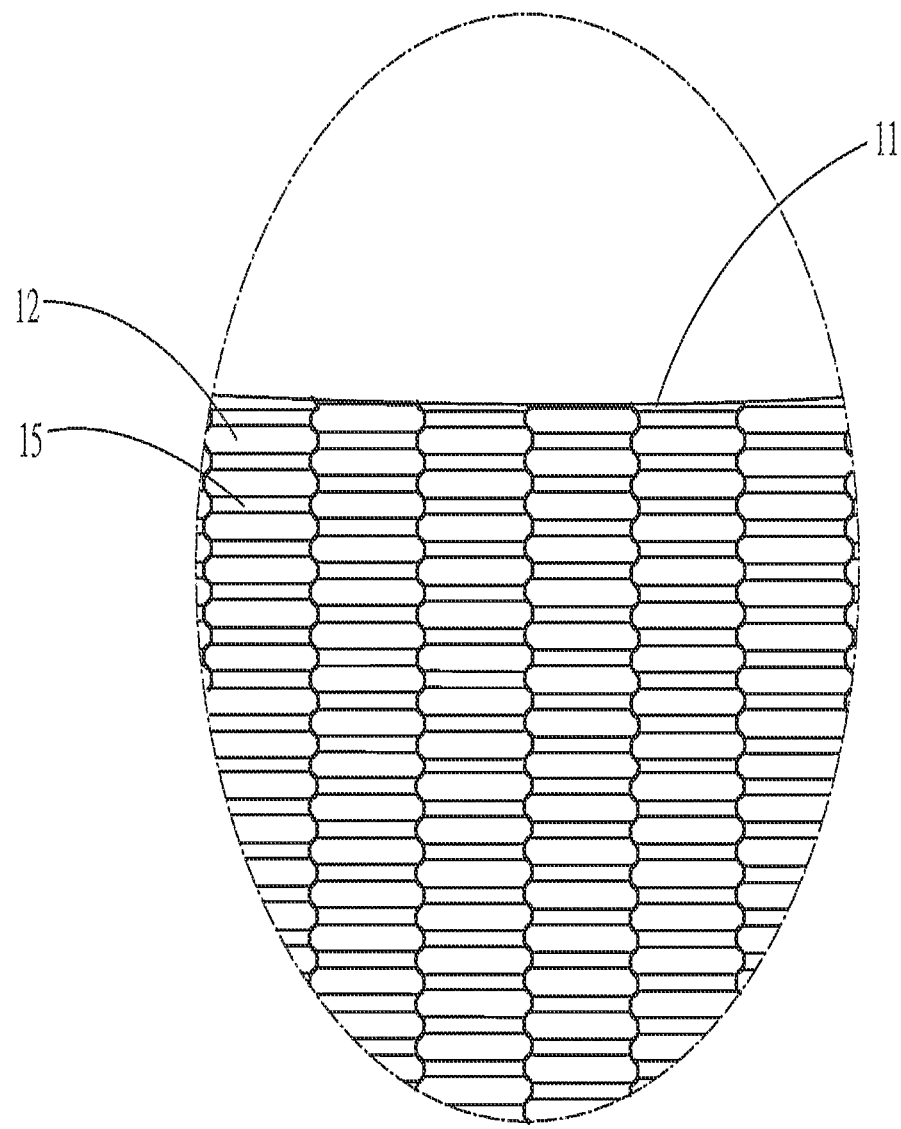
FIG. 6 is a detailed view of the area in circle B of FIG. 5.

Referring to FIGS. 5 to 6 in conjunction with FIG. 4, a user exerts a force along length of the elastic band 10 by pulling its two short edges of the elastic band 10. The elastic band 10 extends lengthwise in opposite directions (see arrows of FIG. 5). Thus, the uneven surfaces 11 are deformed to exert a force on the first uneven zones 12 which in turn are deformed to extend its length. The first inclined edges 13 are closer due to the extension. At this time, a plurality of widthwise, curved lines are formed on either surface of the elastic band 10. The widthwise, curved lines are perpendicular to the extension direction of the elastic band 10.

Figure 7:
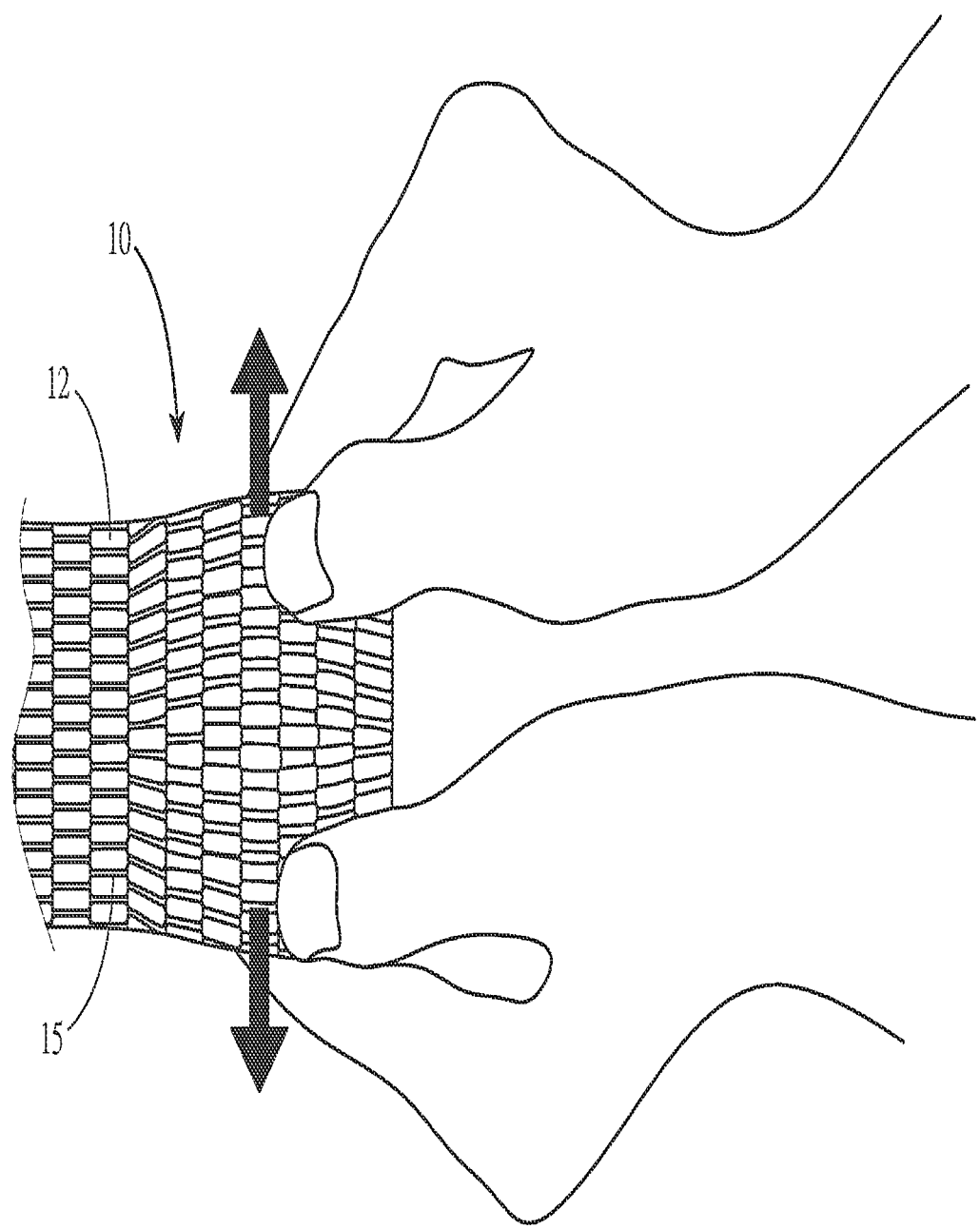
FIG. 7 schematically depicts the tourniquet being extended in response to a pulling force exerted widthwise.

Referring to FIG. 7 in conjunction with FIG. 4, the user exerts a force along width of the elastic band 10 by pulling its two long edges of the elastic band 10. One drawback is that the exertion of force is not easy. But the first uneven zones 12 are deformed to extend its width. Likewise, the first inclined edges 13 are deformed to extend its width. As a result, there is no significant unevenness on either surface of the elastic band 10.

Figure 8:
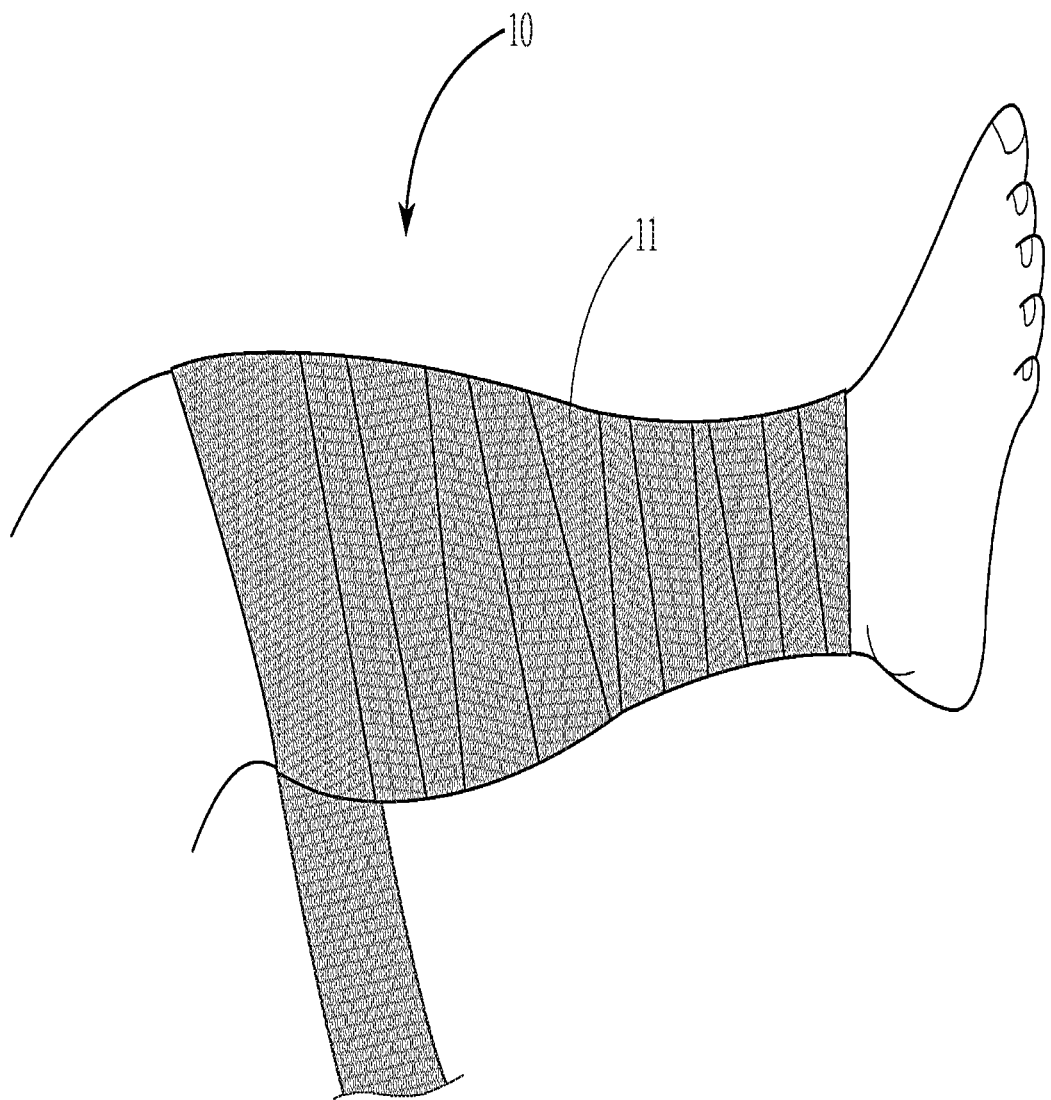
FIG. 8 schematically depicts the leg being wrapped around by the tourniquet.
Figure 9:
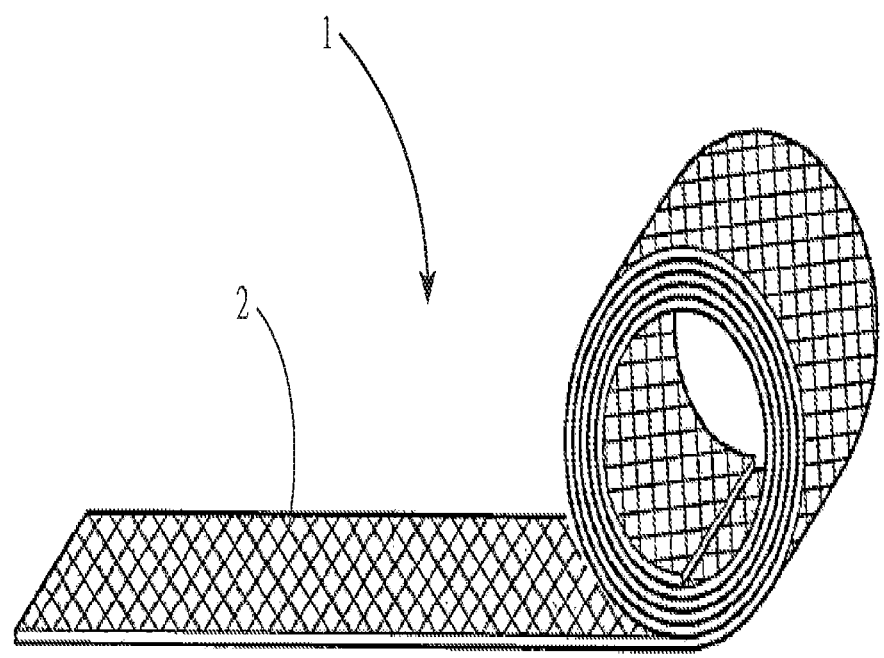
FIG. 9 is a perspective view of a conventional tourniquet.

Referring to FIG. 8 in conjunction with FIGS. 4 to 6, the elastic band 10 can be dyed to have one of a plurality of different colors each corresponding to a body part of the user. For example, the elastic band 10 can be dyed in blue and wrapped around the arm of the user as a tourniquet. Alternatively, the elastic band 10 can be dyed in white and wrapped around the leg of the user as a tourniquet. Force is exerted on a lengthwise direction of the elastic band 10 when the elastic band 10 is fastened. And in turn, the first inclined edges 13 become more uneven and the uneven surfaces 11 also become more uneven. This can increase slip resistance of the tourniquet. Thus, the user may lengthwise pull the elastic band 10, wrap the elastic band 10 around the body part (e.g., the leg) of the user (or a patient), and tie another elastic band 10 around one open end of the elastic band 10 to finish the application of the tourniquet to the body part.

Preferably, width of the elastic band 10 is between 1 cm and 13 cm and thickness thereof is between 0.02 cm and 0.1 cm. The width of the elastic band 10 can be varied based on the body part that the tourniquet to be applied to. The elastic band 10 can cut into a desired size prior to use. The used elastic band 10 can be discarded to prevent it from being used again.

While the invention has been described in terms of preferred embodiments, those skilled in the art will recognize that the invention can be practiced with modifications within the spirit and scope of the appended claims.

What is claimed is:

1. A tourniquet comprising:
an elastic band comprising top and bottom surfaces including an uneven surface on each of the top and bottom surfaces, the uneven surfaces and the elastic band being formed integrally, each of the uneven surfaces including a plurality of rows of a plurality of spaced first uneven zones and a plurality of rows of a plurality of spaced second uneven zones, the spaced first uneven zones being disposed between two adjacent spaced second uneven zones, and each of the spaced second uneven zones being disposed between two adjacent spaced first uneven zones;
wherein each of the spaced first uneven zones are substantially rectangular and concave toward the centers of each of the plurality of spaced first uneven zones; each of the spaced first uneven zones include two raised, opposite first inclined edges, two raised, opposite second inclined edges, and four corners; wherein a length of each of the second inclined edges is greater than that of each of the first inclined edges; wherein a height of each of the first inclined edges is greater than that of each of the second inclined edges; the second inclined edges and the elastic band are oriented lengthwise; the second inclined edges are parallel to one another; an extent of an elastic deformation of each of the second inclined edges is greater than that of each of the first inclined edges; each of the spaced second uneven zones are surrounded by two second inclined edges of two adjacent spaced first uneven zones of the same row and two first inclined edges of two adjacent spaced first uneven zones of two spaced rows of the spaced first uneven zones; the spaced second uneven zones are substantially rectangular and concave towards the centers of each of the plurality of spaced second uneven zones; each of the second uneven zones include two raised, opposite third inclined edges and two raised, opposite fourth inclined edges; a plurality of first ridges formed between each of the first inclined edges and the third inclined edges; a plurality of second ridges formed between each of the second inclined edges and the fourth inclined edges; a height of each of the first ridges is greater than that of each of the second ridges; a length of each of the fourth inclined edges is greater than that of each of the third inclined edges; each of the spaced first uneven zones have a first depth; each of the spaced second uneven zones has a second depth; and the first depth is greater than the second depth.

2. The tourniquet of claim 1, wherein a length of each of the third inclined edges is less than that of each of the first inclined edges, a length of each of the fourth inclined edges is less than that of each of the second inclined edges, and a length of each of the fourth inclined edges is greater than that of each of the first inclined edges.

3. The tourniquet of claim 1, wherein the elastic band is elongated.

4. The tourniquet of claim 1, wherein the uneven surfaces and the elastic band are formed of synthetic rubber.

5. The tourniquet of claim 1, wherein the corners of the spaced first uneven zones are curved.

6. The tourniquet of claim 1, wherein a width of the elastic band is between 1 cm and 13 cm.

7. The tourniquet of claim 1, wherein a thickness of the elastic band is between 0.02 cm and 0.1 cm.

8. The tourniquet of claim 1, wherein the elastic band is blue or white.

* * * * *